United States Patent [19]

Mandon

[11] Patent Number: 4,505,429
[45] Date of Patent: Mar. 19, 1985

[54] DISPENSER FOR AIR TREATING MATERIAL

[75] Inventor: Jean-Pierre Mandon, Chasseneuil-du-Poitou, France

[73] Assignee: Airwick Industries, Inc., Carlstadt, N.J.

[21] Appl. No.: 476,079

[22] Filed: Mar. 17, 1983

[30] Foreign Application Priority Data

Mar. 26, 1982 [CH] Switzerland ............... 1885/82
May 27, 1982 [CH] Switzerland ............... 3268/82

[51] Int. Cl.$^3$ .................................................. A61L 9/12
[52] U.S. Cl. ............................................................ 239/56
[58] Field of Search ................................. 239/34, 53-60

[56] References Cited

U.S. PATENT DOCUMENTS 3,727,840 4/1973 Nigro ........................ 239/57 X
4,247,042 1/1981 Schimanski et al. ............ 239/43
4,423,824 1/1984 Varndell ..................... 239/60 X

FOREIGN PATENT DOCUMENTS 1231135 9/1960 France .
 78461 6/1962 France .
1316894 12/1962 France .

Primary Examiner—Andres Kashnikow
Attorney, Agent, or Firm—Harry Falber

[57] ABSTRACT

The present invention provides a dispenser for an air treating material from which vapors are released into the ambient air through an annular aperture from a round dished base, said dispenser comprising a round dished cover made of an elastic material the top of which curves concavely inwards by exerting pressure on its center, thereby simultaneously exposing the annular aperture, and which curves convexly outwards by exerting pressure on the periphery, thereby closing the annular aperture; a spindle in the center of the inner wall of the dished cover which spindle traverses a bracket secured to two adjacent positions of the dished base; a pad of absorbent material positioned beneath the bracket containing in the interior thereof a plastic sachet which is impermeable to liquid and which contains a volatile active product in liquid form; the exertion of pressure on the center of the cover pushing the spindle downwards so that its tip penetrates the pad beneath the elastic bracket and pierces the plastic sachet in the pad thereby permitting the active liquid product to be absorbed by the pad.

3 Claims, 5 Drawing Figures

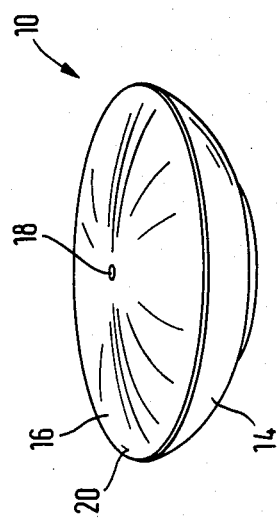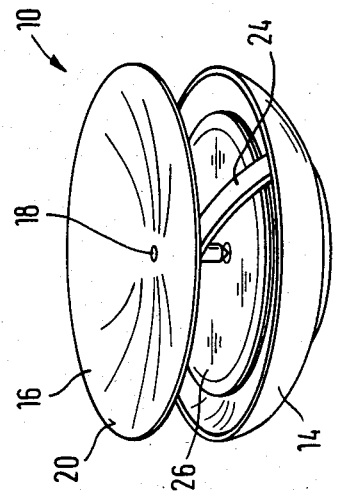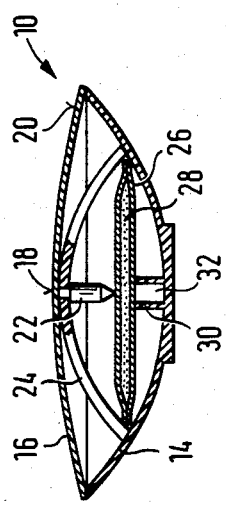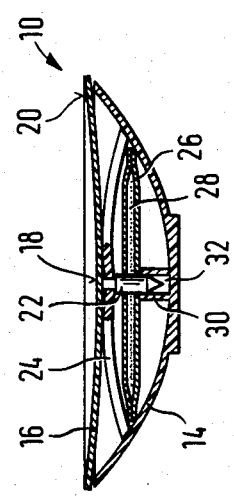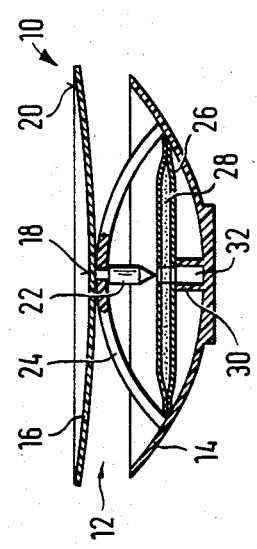

DISPENSER FOR AIR TREATING MATERIAL

The present invention relates to a dispenser for air treating material in the form of an absorbent material which is impregnated with a volatile substance and is contained in a sealable container.

Such dispensers are already known, e.g. from U.S. Pat. No. 4,014,501. The dispenser disclosed therein comprises a cover and a base with apertures in the sidewall for the admission of air and, within, supports for a disc of air treating material. Projections provided at the inner surface of the sidewall segments of the base engage in oblique grooves of the cover and, when the cover is rotated relative to the base, cause a raising or lowering of the cover, whereby the apertures are partially or substantially exposed and the emission of the volatilising substance can be controlled.

A dispenser for air treating material is also known which comprises a dished cover of elastic material on a dished base, said base being secured at its centre to an elastic bracket supported at two adjacent positions of the inner sidewall of the base. Located between cover and base is a ring or disc with air treating material. When pressure is exerted on the centre of the container, the cover curves concavely inwards and exposes an annular aperture between cover and base, so that the volatile air treating material is released. To close the annular aperture, pressure is exerted on the periphery of the cover which curves convexly outwards and again lies with its edge flush with the edge of the dished base. The shortcoming of both dispensers is the requirement of a material which is impregnated with moist air treating material. To ensure easy opening, the covers of the dispensers are unable to close tightly enough to prevent the volatilisation of a portion of the air treating material. Especially during long storage in commercial use, the odour of the air treating material becomes very noticeable and gradually the material is used up before the article is sold.

This shortcoming is overcome by the dispenser of the present invention through the absorbent material not being activated or impregnated with the air treating material until immediately before use of the dispenser by the consumer.

The above, and other objects, features and advantages of this invention will be apparent in the following detailed description of an illustrative embodiment thereof which is to be read in connection with the accompanying drawings, wherein:

FIG. 1 is an elevated, cross-sectional view of a dispenser for air treating material according to the instant invention showing the dispenser in closed position;

FIG. 2. is an elevated cross-sectional view of the dispenser, showing said dispenser when pressure is exerted on the center of the cover;

FIG. 3. is an elevated, cross-sectional view of the dispenser, showing said dispenser in open position;

FIG. 4. is a perspective view of the dispenser showing it in closed position; and FIG. 5. is a perspective view of the dispenser showing it in opened position.

Accordingly, the present invention provides a dispenser 10 for an air treating material from which vapours are released into the ambient air through an annular aperture 12 from a round dished base 14, said dispenser 10 comprising a round dished cover 16 made of an elastic material the top of which curves concavely inwards by exerting pressure on its centre 18, thereby simultaneously exposing the annular aperture 12, and which curves convexly outwards by exerting pressure on the periphery 20, thereby closing the annular aperture 12 again, said dished cover 16 being provided with a spindle 22 in the centre of the inner wall thereof, which spindle 22 traverses a bracket 24 which is made of elastic material and which is secured to two adjacent positions of the dished base, and there being present beneath said bracket 24 a pad 26 of absorbent material containing in the interior thereof a plastic sachet 28 which is impermeable to liquid and which contains a volatile active product in liquid form.

Preferably, the pad 26 is located on a support 30 having a central aperture 32 which is so dimensioned that it admits the spindle 22 beneath the bracket 24 when pressure is exerted on the centre of the cover 16 and after the pad 26 has been pierced.

The dispenser of this invention functions by exerting pressure on the centre of the cover, whereby pressure is simultaneously exerted on the elastic bracket extending across the dished base, such that the spindle is pushed downwards and its tip penetrates the pad beneath the bracket. The plastic sachet which is impermeable to liquid in the pad is pierced, so that the liquid gradually flows out and is absorbed by the absorbent pad. When the centre of the cover is depressed, the cover simultaneously curves concavely inwards and so exposes the annular aperture at the edge of the dispenser, whereby volatile air treating material is able to be released. Preferably, the pad rests on a support having a central aperture. After the pad has been pierced, this aperture admits the tip of the spindle or the spindle itself and thus acts as its abutment.

After pressure has been briefly exerted on the centre of the cover and the pad has been pierced, the spindle is raised once more to its starting position by the elastic bracket and the cover remains open. Only by exerting pressure on the periphery of the cover does this latter again curve convexly outwards and thereby close the annular aperture at the edge of the dispenser.

What is claimed is:

1. A dispenser for an air treating material from which vapours are released into the ambient air through an annular aperture from a round dished base, said dispenser comprising a round dished cover made of an elastic material the top of which curves concavely inwards by exerting pressure on its centre, thereby simultaneously exposing the annular aperture, and which curves convexly outwards by exerting pressure on the periphery, thereby closing the annular aperture again, said dished cover being provided with a spindle in the centre of the inner wall thereof, which spindle traverses a bracket which is made of elastic material and which is secured to two adjacent positions of the dished base, and there being present beneath said bracket a pad of absorbent material containing in the interior thereof a plastic sachet which is impermeable to liquid and which contains a volatile active product in liquid form.

2. A dispenser according to claim 1, wherein the pad is located on a support having a central aperture.

3. A dispenser according to claim 2, wherein the central aperture is so dimensioned that it admits the spindle beneath the bracket when pressure is exerted on the centre of the cover and after the pad has been pierced.

* * * * *